United States Patent [19]
Pomato et al.

[11] Patent Number: 5,595,738
[45] Date of Patent: Jan. 21, 1997

[54] CTAA 81AV78, THE ANTIGEN RECOGNIZED BY HUMAN MONOCLONAL ANTIBODY 81AV78

[75] Inventors: Nicholas Pomato, Frederick, Md.; Janet H. Ransom, Shepardstown, W. Va.

[73] Assignee: Akzo Nobel N.V., Arnhem, Netherlands

[21] Appl. No.: 150,036

[22] PCT Filed: May 15, 1992

[86] PCT No.: PCT/US92/04108

§ 371 Date: Dec. 6, 1993

§ 102(e) Date: Dec. 6, 1993

[87] PCT Pub. No.: WO92/20374

PCT Pub. Date: Nov. 26, 1992

Related U.S. Application Data

[63] Continuation-in-part of Ser. No. 701,252, May 16, 1991, abandoned.

[51] Int. Cl.$^6$ .......................... A61K 31/20; A61K 34/38
[52] U.S. Cl. .................... 424/184.1; 424/277.1; 530/388.8; 435/7.23; 436/71
[58] Field of Search ................ 424/88, 277.1, 424/184.1; 530/388.8; 435/7.23; 436/71

[56] References Cited

U.S. PATENT DOCUMENTS

| | | | |
|---|---|---|---|
| 4,471,057 | 7/1984 | Koprowski et al. | 436/518 |
| 4,666,845 | 5/1987 | Mattes et al. | 435/240 |
| 5,011,920 | 4/1991 | Hakomori et al. | 536/53 |
| 5,348,880 | 9/1994 | Hanna et al. | 435/240.27 |

OTHER PUBLICATIONS

Pomato et al. 1991. Identification and Characterization of a lipid antigen . . . Proceedings of Am. Association. Cancer Res. vol. 32 Mar. 1991, Abs. #1439.

Makidono et al. The Predictive Value of the Anti-Cardiolipin Antibody Test . . . Nippon Igaku Hoshasen Gakkai Zasshi 51:44–50.

Roitt et al. 1985, Immunology C. V. Mosby Company, pp. 18.1, 18.13–18.15.

Paul et al. 1989, Fundamental Immunology, pp. 923, 944–947.

Fenwick et al. 1989, Biodistribution and Histological Localization of Anti–Human Colon . . . 44:1017–27.

Lando et al. 1982 The Lipid Nature of a Tumor–Associated Autoantigen . . . Scand. J. Immunol. 14:187–193.

Berzofsky et al. 1989. Immunogenicity and Antigen Structure Fundamental Immunology 2nd Editiion. pp. 169–201.

Higashi et al. 1985. Characterization of N–Glycolylneuraminic Acid–containing . . . Cancer Res. 45:3796–3802.

Kaizu et al. 1986, Novel Fucolipid of Human Adenocarcinoma: Monoclonal Antibody . . . 261(24):11254–258.

Magnani et al. 1982. A Monoclonal Antibody–defined Antigen Associated with Gastrointestinal . . . JBC 257(23):14365–14369.

Silverberg, E., "Cancer Statistics", CA (1983) 33:9–25.

Goligher, J. C., *Surgery of the Anus, Rectum and Colon*, 4th ed., London: Baillere Tindall (1980) 470–471.

Hoover, H. C., Jr., et al., "Prospectively Randomized Trial of Adjuvant Active–Specific Immunotherapy for Human Colorectal Cancer", *Cancer* (1985) 55:1236–1243.

Gold, P. and Freedman, S. O., "Specific Carcinoembryonic Antigens of the Human Digestive System", *J. Exp. Med.* (1965) 122:467–481.

Yeoman, L. C. et al., "Human Colon Tumor Antigens", *Methods in Cancer Research*, vol. 19, 231–271, New York: Academic Press, Inc. (1982).

Magnani, J. L. et al., "Identification of the Gastrointestinal and Pancreatic Cancer–associated Antigen Detected by Monoclonal Antibody 19–9 in the Sera of Patients as a Muchin", *Cancer Res.* (1983) 43:5489–5492.

Artigas, C. et al., "Identification of a $M_r$ 40,000 Polypeptide from Colorectal Cancer Which Expresses Organ–specific Cancer Neoantigen Activity as Determined by Leukocyte Adherence Inhibition", *Cancer Res.* (1986) 45:1874–1881.

Blaszcyzk, M., et al., "Characterization of Gastrointestinal Tumor–associated Carcinoembryonic Antigen–related Antigens Defined by Monoclonal Antibodies", *Cancer Res.* (1984) 44:245–253.

Ross, A. H., et al., "Isolation and Characterization of a Carcinoma–Associated Antigen", *Biochem. Biophys. Res. Comm.* (1986) 135:297–303.

Haspel, M. V. et al., "Generation of Tumor Cell–reactive Human Monoclonal antibodies Using Peripheral Blood Lymphocytes from Actively Immunized Colorectal Carcinoma Patients", *Cancer Res.* (1985) 45:3951–3961.

Hoover, et al., "Immunotherapy by Active Specific Immunization:Clinical Applications", *Biologic Therapy of Cancer Principles and Practices*, (1990) In press. J. P. Lippincott Co.

Kaizu et al., "Novel Fucolipids of Human Adenocarcinoma: Monoclonal Antibody Specific for Trifucosyl Le$^y$ (III$^3$FucV$^3$FucVI$^2$FucnLc$_6$) and a Possible Three–dimensional Epitope Structure", *J. Biol. Chem.*, 24:11254–11258.

Magnani, J. L. et al., "A Monoclonal Antibody–defined Antigen Associated with Gastrointestinal Cancer is a Ganglioside Containing Sialylated Lacto–N–fucopentaose II", *J. Biol. Chem.*, 257:14365–14369 (1982).

Higashi, H. et al., "Characterization of N–Glycolylneuraminic Acid–containing Gangliosides as Tumor–associated Hanganutziu–Deicher Antigen in Human Colon Cancer", *Cancer Research*, 45:33796–3802 (1985).

Berzofsky, J. A. et al., "Immunogenicity and Antigen Structure", *Fund. Immuno. Second Edition*, pp. 185–188 (1989).

(List continued on next page.)

*Primary Examiner*—James C. Housel
*Assistant Examiner*—N. M. Minnifield
*Attorney, Agent, or Firm*—Mary E. Gormley; William M. Blackstone

[57] ABSTRACT

A lipid antigen found in colon, breast, lung, ovarian and pancreatic human adenocarcinomas identified by reactivity with human monoclonal antibody 81AV78, and the use of the antigen in vaccines.

5 Claims, 14 Drawing Sheets

OTHER PUBLICATIONS

Pomato, N. et al., "Identification and Characterization of a Lipid Antigen, CTAA 81AV78, Recognized by a Tumor Reactivie Human Monoclonal Antibody", Proceedings of the American Association for Cancer Research Annual Meeting, vol. 32, p. 242, Abstract 1439.

Roitt, I. M., et al., "Immunology," published 1985 by C. V. Mosby Company, pp. 18.1, 18.13–18.15.

Paul, W. E., "Fundamental Immunology", published 1989 by Raven Press, pp. 923, 944–947.

Fenwick, J. R. et al., "Biodistriction and Histological Localization of Anti–Human Colon Cancer Monoclonal Antibody (Mab)1A3: The Influence of Administered Mab Dose on Tumor Uptake", 44:1017–1027 (1989).

Makidono et al., "The Predictive Value of the Anti–Cardiolipin Antibody Test for Malignant Tumors", *Nippon Igaku Hoshasen Gakkai Zasshi*, 51: pp. 44–50.

Lando et al., "The Lipid Nature of a Tumour–Associated Autoantigen from a Chemically Induced Rat Hepatoma", *Scan. J. Immunolo.*, 14:187–193 (1982).

Pomato et al., "Identification and Characterization of a Lipid Antigen, CTAA 81AV78, Recognized by a Tumor Reactive Human Monoclonal Antibody," *Proceedings of the American Association for Cancer Research,* 32:Abstract 1439 May 1991, p. 242.

Murray et al., "Immunohistochemical Characterization of Tissue Reactivity of Two Tumor Reactive Human Monoclonal Antibodies," *Proceedings of the American Association for Cancer Research,* 33:Abstract 2030, Mar. 1992, p. 340.

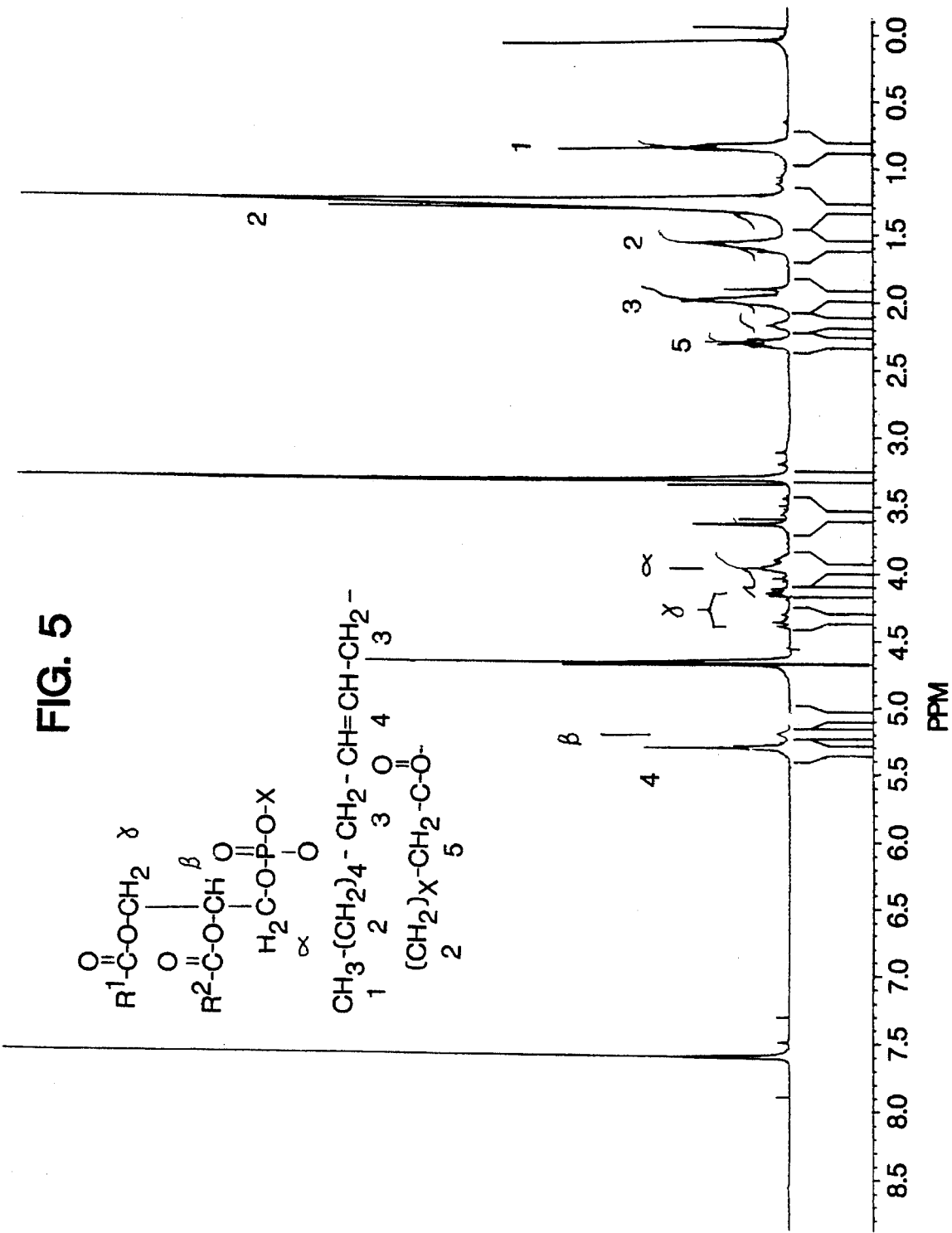

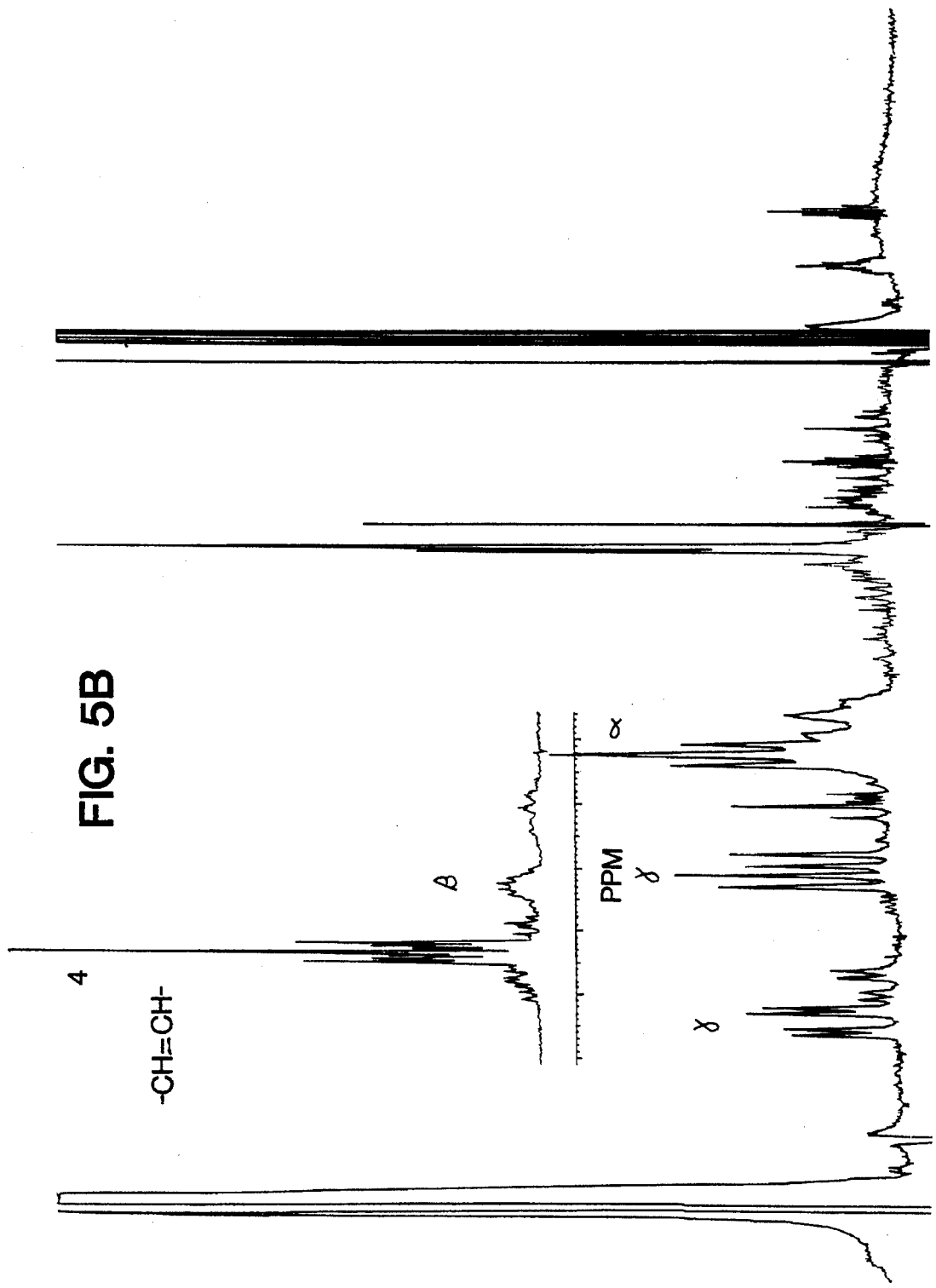

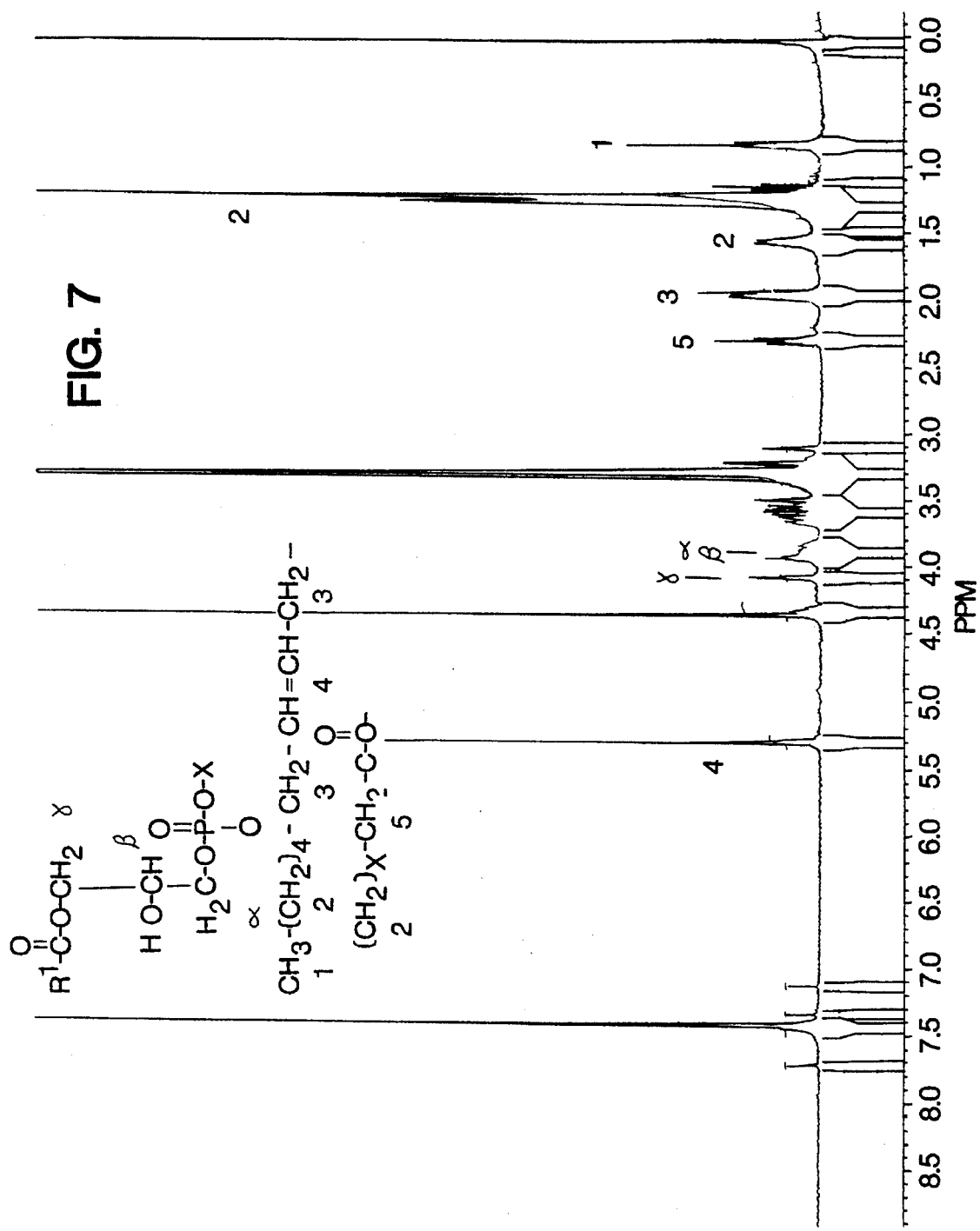

CTAA 81AV78, THE ANTIGEN RECOGNIZED BY HUMAN MONOCLONAL ANTIBODY 81AV78

This application is a national phase of PCT/US92/04108 filed May 15, 1992, which is a continuation-in-part of U.S. Ser. No. 07/701,252, filed May 16, 1991 now abandoned.

BACKGROUND OF THE INVENTION

Colorectal cancer is the second most prevalent cancer in the United States, affecting both men and women. Until recently, the only viable treatment for this disease has been surgery, which has a poor prognosis for patients with transmural extension of tumor and metastasis to regional lymph nodes. A dramatically improved prognosis was indicated in a recently reported randomized Phase II-active specific immunotherapy trial, which showed that immunization of patients with autologous tumor cells admixed with Tice BCG (Bacillus Calmette Guerin) (Institute for Tuberculosis Research, Chicago, Ill.) significantly increased delayed cutaneous hypersensitivity responses and, over a four year period of time, significantly decreased recurrence and mortality.

There have been numerous publications describing the identification of colon carcinoma-associated antigens. The majority of these antigens were identified using monoclonal antibodies generated by immunizing mice with some form of the colon tumor (extracts, dissociated cells, membrane preparations, and etc.) or colon tumor cell lines. These mouse antibodies identify a repertoire of antigens that were antigenic in the mouse. In addition to these studies, there are several reports of human monoclonal antibodies that show specific reactivity with tumor material.

Using peripheral blood B-cells from colorectal patients actively immunized with autologous tumor cells and BCG in immunotherapy protocols, we have successfully developed a strategy for producing human anti-tumor monoclonal antibodies. Unlike mouse monoclonal antibodies generated against human colon cancer, which often recognize tissue components also found in healthy individuals, such as CEA, our human monoclonal antibodies exhibit no reactivity with CEA, blood group determinants or histocompatibility antigens, indicating that these antibodies are characterized by a specificity confined to those epitopes that are recognized as immunogenic in the autologous host.

We have used these human monoclonal antibodies as probes to identify tumor antigens. We have identified a particular antigen in colon tumors, extracts of colon tumor cell lines and human tumor xenografts generated in nude mice. The subject antigen is characterized by containing an epitope recognized by human monoclonal antibody (MCA) 81AV78.

SUMMARY OF THE INVENTION

CTAA 81AV78 is a tumor associated antigen recognized by the human monoclonal antibody 81AV78 claimed in copending application U.S. Ser. No. 07/701,281 filed May 16, 1991 for Tumor Associated Monoclonal Antibody 81AV78, by Hanna et al., and included herein by reference. This IgM monoclonal antibody is found to be reactive with a cell surface antigen in various tumor cell lines. CTAA 81AV78 is found in lipid extracts of colon tumor cell lines, primary colon tumors, and colon tumor xenograft tissues. The antigen has been found to be acidic in nature and can be purified by various thin layer chromatographic and column chromatographic techniques.

The invention also relates to the use of antibodies to the antigen containing this epitope for diagnosis and monitoring of treatment of cancer and to the use of this antigen in the preparation of vaccines to elicit an immune response similar to that obtained against tumor cells containing this epitope.

BRIEF DESCRIPTION OF THE DRAWINGS

FIG. 5 is the NMR spectrum of CTAA 81AV78-4A. FIG. 5B is an expansion of the NMR of FIG. 5, and better shows the alpha and gamma resonances between about 3.5 and 4.5 PPM (the insert in FIG. 5B shows the beta resonances between about 5.5 and 5.0 on FIG. 5).

FIG. 7 shows the NMR Spectrum of CTAA 81AV78-5.

DESCRIPTION OF THE PREFERRED EMBODIMENTS

We have found the antigen recognized by human MCA 81AV78 in colon, breast, lung, ovarian and pancreatic adenocarcinomas through cell surface binding to tumor cells by indirect live cell fluorescence. No relationship between antigen expression and cell cycle was evident. These results are presented in Table 4.

Lipids from colon tumor cell lines and primary colon tumors have been found to be reactive with the human monoclonal antibody 81AV78. The lipids were purified by column chromatography and thin layer chromatographic methods. The purified lipids were found to be acidic phospholipids that did not appear to be glycosylated. Two lipids comprising the antigen were identified and characterized by their migration in various thin layer chromatographic systems. Since at least one of the two lipids causes proliferation of T-cells, this antigen is a good candidate for use in a vaccine to elicit cell mediated immune responses to various types of cancer.

Extraction and Purification of CTAA 81AV78

Crude lipids were extracted from tumor cell lines or primary colon tumors using chloroform-methanol extraction (2:1). The crude lipid fraction was found to have immunoreactive spots when tested in one dimensional thin layer chromatography. Separation of the neutral from the acidic lipids using DEAE Sephadex anion exchange chromatography indicated that the immunoreactive lipids were found in the lipids that bound to this column. Thus, the immunoreactive lipids were located in the acidic pool of lipids after extraction and fractionation.

The immunoreactive lipids recognized by the human monoclonal antibody 81AV78 have been designated CTAA 81AV78-4A and CTAA 81AV78-5. Using two dimensional thin layer chromatography it has been found that both of these antigens are present in tumor tissue extracts but were not found in normal colon extracts. They are absent from normal tissue or are present only in small quantities of marginal detectability. FIG. 1 shows the results of two sets of tumor tissues and normal colon tissues that had been extracted and analyzed by two dimensional TLC using chloroform-methanol solvent in the first dimension and butanol-pyridine solvent in the second dimension. Various spots were identified on these chromatograms by charring.

Figure 1A:
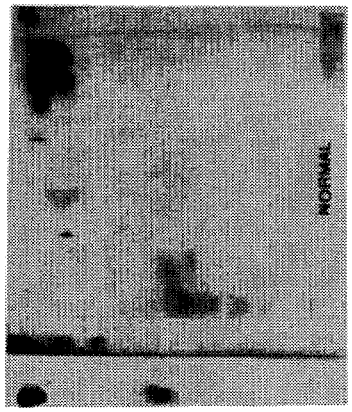
FIGS. 1A–1D show two dimensional TLC of two sets of tumor FIGS. 1C and 1D) and normal tissue (FIGS. 1A and 1B). These figures show the CTAA 81AV78-4A and CTAA 81AV78-5 are present in tumor tissue extracts but were not found in normal colon tissue extract.
Figure 1B:
Figure 1C:
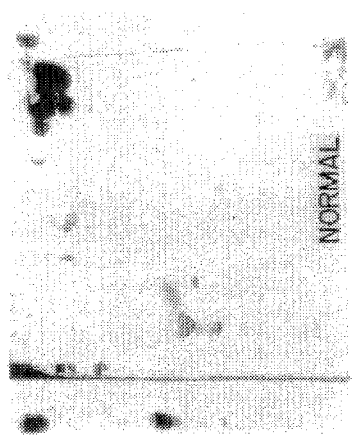
Figure 1D:
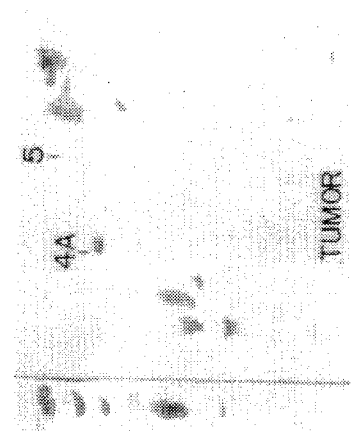
Figure 2:
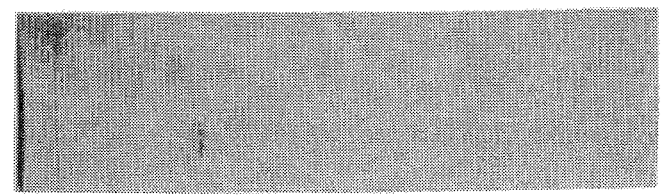
FIG. 2 Purity of CTAA 81AV78-4A and 5 By TLC.

The two acidic lipids were purified to apparent homogeneity after extraction from tumor cell lines using anion exchange chromatography followed by preparative thin layer chromatography. Table 5 reports the relative quantity of the two lipids purified from eight different tumor cell lines obtained from the American Type Culture Collection, which indicates that most tumor cell lines showed sufficient expression of these lipids such that they could be purified from cellular material. The solvent system used for purification was the butanol-pyridine system. Lipids were cut out from thin layer chromatograms and eluted from the silica gel with chloroform-methanol. As shown in FIG. 2, when the extracted lipids were rechromatographed a single spot was obtained for each of the lipids.

Figure 3:
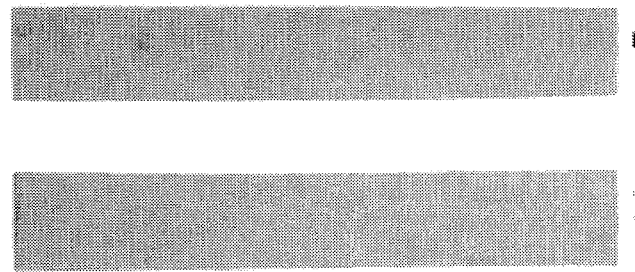
FIG. 3 Immunoreactivity of CTAA 81AV78-4A and 5 With MCA 81AV78.

The purified lipids were then rechromatographed and examined for immunoreactivity with MCA 81AV78. As shown in FIG. 3, immunoreactive spots were observed for both the CTAA 81AV78-4A and the CTAA 81AV78-5.

In order to further characterize the two lipid antigens, both antigens were subjected to thin layer chromatography in multiple solvent systems. The antigens were tested both in purified and in crude acidic form. Table 1A summarizes the $R_f$ values for CTAA 81AV78-4A in three solvent systems. Table 1B summarizes the $R_f$ values for CTAA 81AV78-5 in the same solvent systems.

In order to further characterize these antigens, two dimensional thin layer chromatography was performed on both the crude acidic pools and the purified antigens. For the crude acidic pools, the first dimension of the chromatogram used a chloroform-methanol solvent system and the second dimension utilized the butanol-pyridine solvent system. For the purified antigen the first dimension used a butanol-pyridine solvent system and the second dimension used a chloroform-methanol solvent system. The $R_f$ values for these antigens after two dimensional electrophoresis are reported in Table 2.

Figure 4:
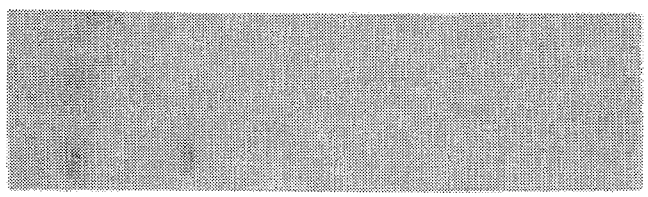
FIG. 4 CTAA 81AV78-4A and 5 purified by thin layer chromatography Are Positive For Phosphate Groups After TLC.

In order to further characterize the nature of the lipid antigens recognized by MCA 81AV78, the antigens were subjected to thin layer chromatography using a chloroform-methanol solvent system and then sprayed with Phospray, which detects phosphorylated lipids. As shown in FIG. 4, both CTAA 81AV78-4A and CTAA 81AV78-5 reacted positively to this spray, indicating that both of these lipids are phosphorylated. Similar experiments using a detection system which could identify potential carbohydrate residues bound to these phospholipids were negative, indicating that neither of the lipids seems to be glycosylated.

One reason for obtaining tumor associated antigens recognized by human monoclonal antibodies is to potentially develop antigens for the generation of a vaccine. In order to validate the potential usefulness of CTAA 81AV78-4A and CTAA 81AV78-5 for this purpose, T-cell proliferative assays were performed on peripheral blood lymphocytes from patients undergoing active specific immunotherapy. As shown in Table 3, CTAA 81AV78-4A elicited T-cell proliferative responses in the PBL of two patients who had been immunized with autologous tumor cells. This indicates that this antigen is a candidate for vaccine development.

EXAMPLE I

Isolation of Antigen

Antigen Sources

The tumor cell lines WiDr and HCT-8 were obtained from the American Type Tissue Culture Collection (ATCC), Rockville, Md. Primary colon tumors were obtained after surgical removal from the Washington Hospital, Washington, D.C.

Thin Layer Chromatographic Techniques

This layer chromatography plates are designated as HPTLC-KIESELEG 60 (EM Sciences, Gibbstown, N.J., Catalog Number 5547). The first solvent system used was: chloroform-methanol, calcium chloride, and ammonium hydroxide at volume ratios of 30:20:3.2 (v/v/v), respectively. The second system used was butanol, pyridine, and 30% ammonium hydroxide solution at volume ratios of 30:47.5:5.75 (v/v/v). A third solvent system used was propanol, hexanol and water at volume ratios of 25:25:3 (v/v/v). In general, samples were spotted onto the chromatographic plates, which were then placed in a chromatography chamber. The solvent migrated upward on the plates by capillary action resulting in resolution of the lipids present. Thin layer chromatograms were visualized by spraying with 10% sulfuric acid followed by heating on a hot plate until visible (maximum temperature approximately 100° C.). The presence of phosphate in the various lipids was determined by spraying with Phospray from Suppelco, Inc. (Catalog Number 3-3047).

Column Chromatographic Techniques

DEAE-Sephadex was obtained from Pharmacia, Inc., Piscatawy, N.J. High performance liquid chromatography SI-60 Silica column was obtained from Suppelco, Inc. For the DEAE Sephadex column, lipid extracts were loaded onto the column, which had previously been equilibrated in 100% methanol. The lipids that stuck to the column were eluted with 100% methanol containing 0.3M ammonium acetate. For the silica SI-60 column, samples were loaded on the column that had previously been equilibrated with propanol-hexanol at a 1:1 ratio. The column was then eluted with a linear gradient of propanol-hexanol containing 4% water to propanol containing 9% water. All solvent buffers contained 0.005% ascetic acid.

Immunoreactivity

Immunoreactivity of the lipid antigen was demonstrated using MCA 81AV78. Approximately 40 μg of purified lipids or 100–20 μg of crude acidic lipids were spotted on TLC plates using the chloroform-methanol solvent system. All solutions used contained 3% polyvinylpyrrolidone (Amresco, Solon, Ohio Catalog Number P0050720). The plates were dried and then blocked with blotto (5% w/v of non-fat dry milk in phosphate buffered saline [PBS]) for 1 hour. After washing 3× in PBS, the plate was incubated with MCA 81AV78 diluted to 10 μg/ml in PBS at 23° C. for 1 hour. After washing 3× with PBS, goat anti-human IgM-peroxidase conjugated (KPL, Rockville, Md.) was diluted 1:1000 and the plate was incubated at 23° C. for 1 hour. After washing 3× with PBS, the plate was developed with 0.06% dimethylaminoazobenzene (Sigma Chemical Co., St. Louis, Mo.) and 0.003% hydrogen peroxide in PBS.

T-cell Proliferation Assays

T-cell proliferative assays were performed using the peripheral blood lymphocytes (PBL) from patients who had been immunized with their own tumor cells. PBL were stored at −70° C. and then thawed and plated in microtiter plates at a density of $5 \times 10^4$ cells per well. The test antigens were added at concentrations of 20 μg to 200 μg per well. Thirty units/ml of gamma-interferon were added per well. Cells were incubated for six days, pulsed for 16 hour with [$^3$H]-thymidine, collected onto filters and counted. The stimulation index (S.I.) was calculated as follows:

$$S.I. = \frac{\text{CPM of Test Antigens}}{\text{CPM of Media Control}}$$

For these experiments, purified protein derivative (PPD) was used as a control.

EXAMPLE II

Analysis of CTAA 81AV78-4A and CTAA 81AV78

CTAA 81AV78-4A and 5 were purified by thin layer chromatography (Merck silica 60; solvent system chloroform:methanol:water=65:25:4, detection: Usui reagent). They were found to contain a contaminating fraction with high Rf (near the solvent front). Each preparation (dissolved in chloroform:methanol=9:1) was chromatographed on a small (0.3×5 cm) column of silica (Merck silica 60: 43–60 μm; equilibrated in chloroform:methanol=9:1). The high Rf material was eluted from the column with the 9:1 eluent and was found by NMR analysis to contain essentially only free fatty acid material. The main antigen component was sub-sequently eluted with chloroform:methanol:water (65:35:4) (fractions 5 and 4A, respectively).

The pure antigen fractions, 5 (CTAA 81AV78-5) and 4A (CTAA 81AV78-4A) were further analyzed by $^1$H-NMR, FAB-MS and fatty acid analysis.

Analysis of 4A

Figure 5A:
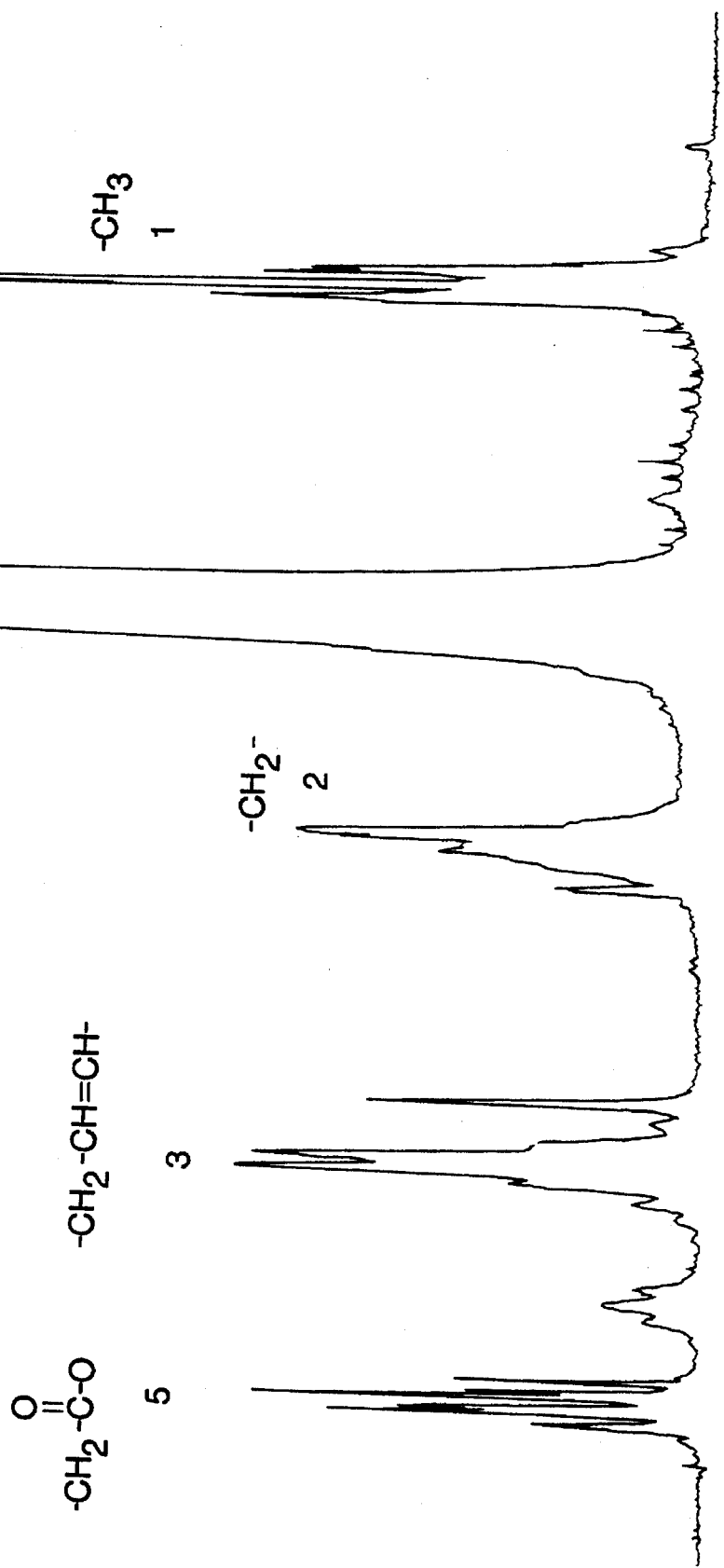
FIG. 5A is an expansion of the NMR of FIG. 5 between about 2.5 and 0.5 PPM to better show the unsaturated fatty acid side chain at 2.0 PPM.

The $^1$H-NMR spectrum of 4A is shown in FIG. 5. The glycerol backbone proton resonances α, β and γ are illustrative of a phosphatidic acid core structure, i.e., both γ- and β-hydroxyl functions are acylated ($R^1$ and $R^2$), while the α-hydroxyl function is phosphorylated.

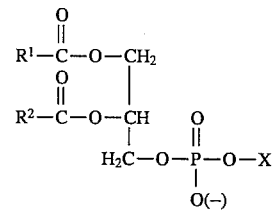

Resonances due to the acyl chains indicate the presence of unsaturated fatty acids: —CH=CH= protons at 5.3–5.4 ppm and the —CH=CH—$\underline{CH}_2$— protons at 2.0 ppm.

Figure 6:
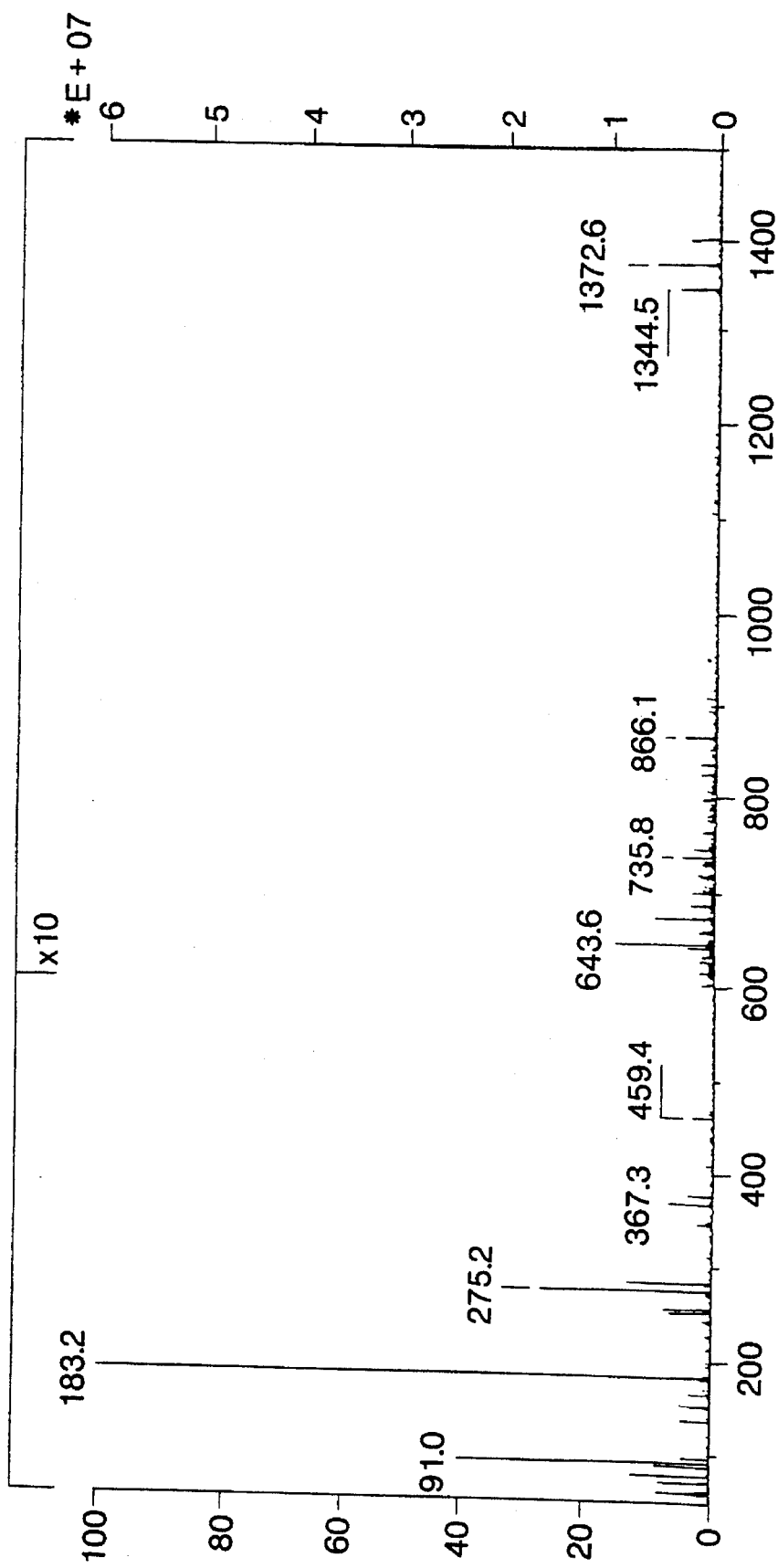
FIG. 6 is the Fast Atom Bombardment (FAB)-Mass Spectrometer Spectra of CTAA 81AV78-4A.
Figure 6A:
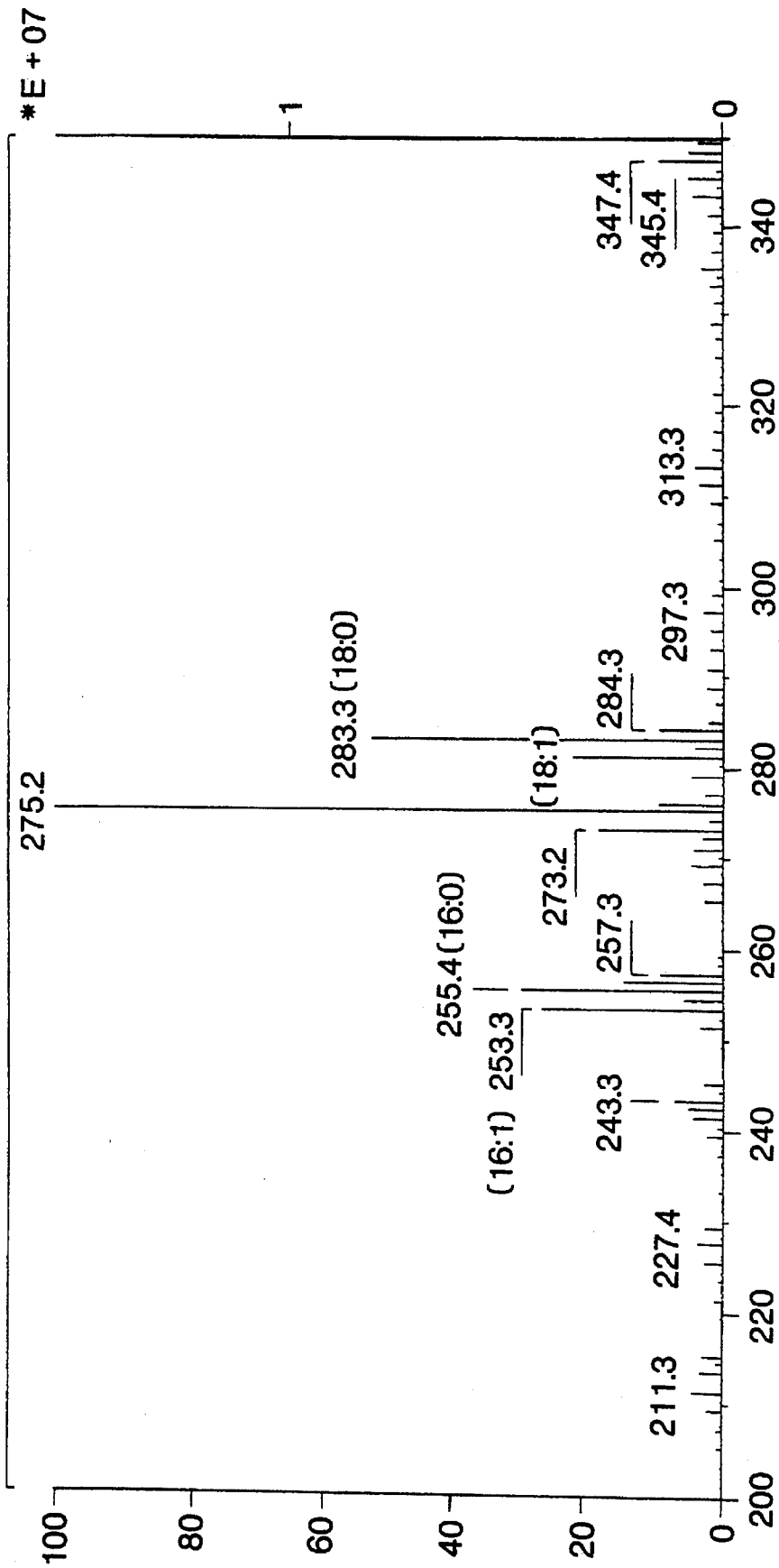
FIG. 6A is an expansion of the region of FIG. 6 between 200 and 350, showing the presence of fatty acids.
Figure 6B:
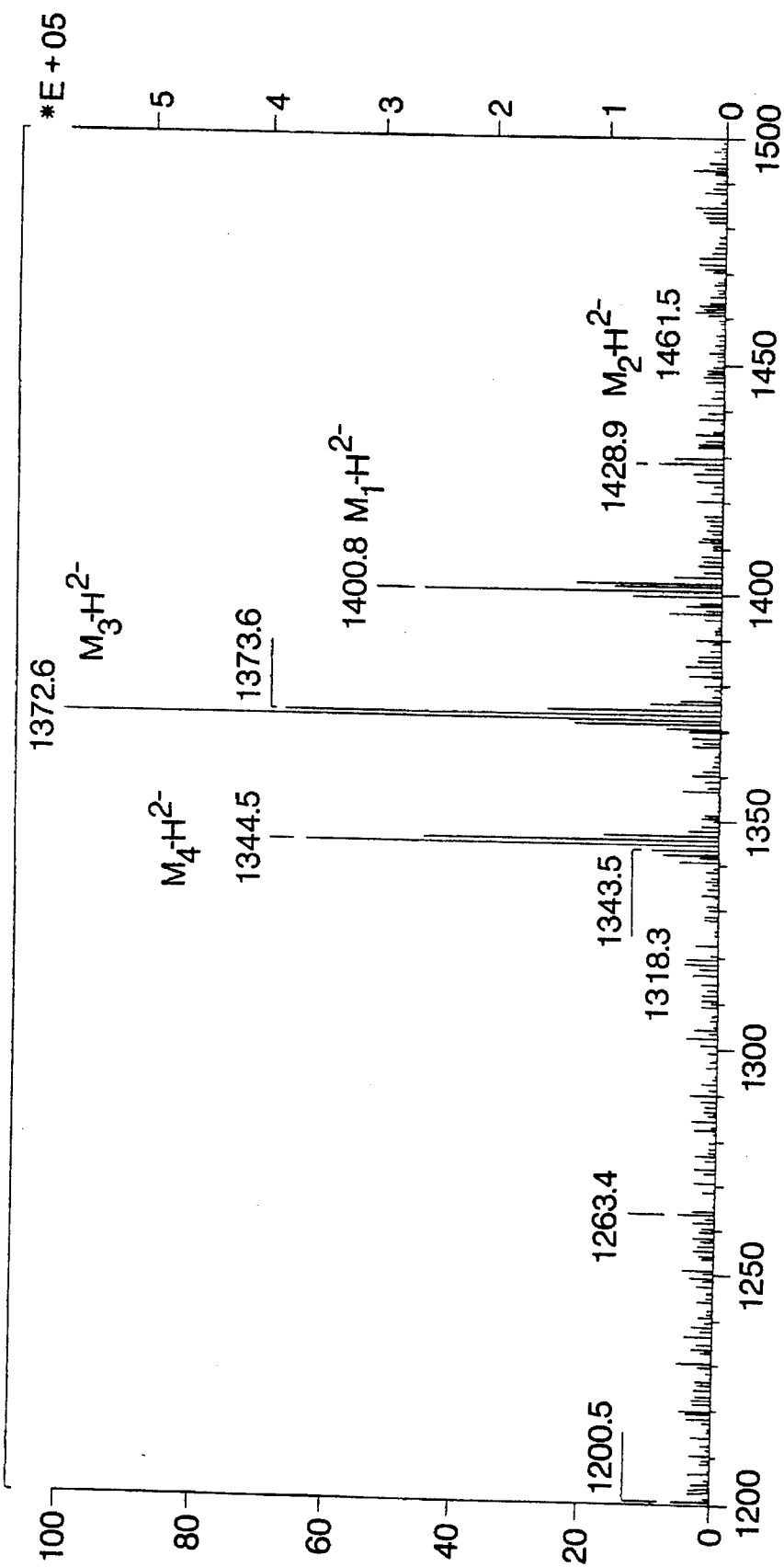
FIG. 6B is an expansion of FIG. 6 between 1200 and 1500, showing the molecular masses in better detail.

FAB-MS spectra, FIG. 6, provided molecular masses of 1344, 1372, 1400 and 1488, and identified the presence of the fatty acids 16:0, 16:1, 18:0 and 18:1.

$^1$H-NMR and FAB-MS data were consistent with diphosphatidylglycerol (cardiolipin) as the main component in antigen 4A, with heterogeneity in the fatty acid part of the molecule.

Figure 9:
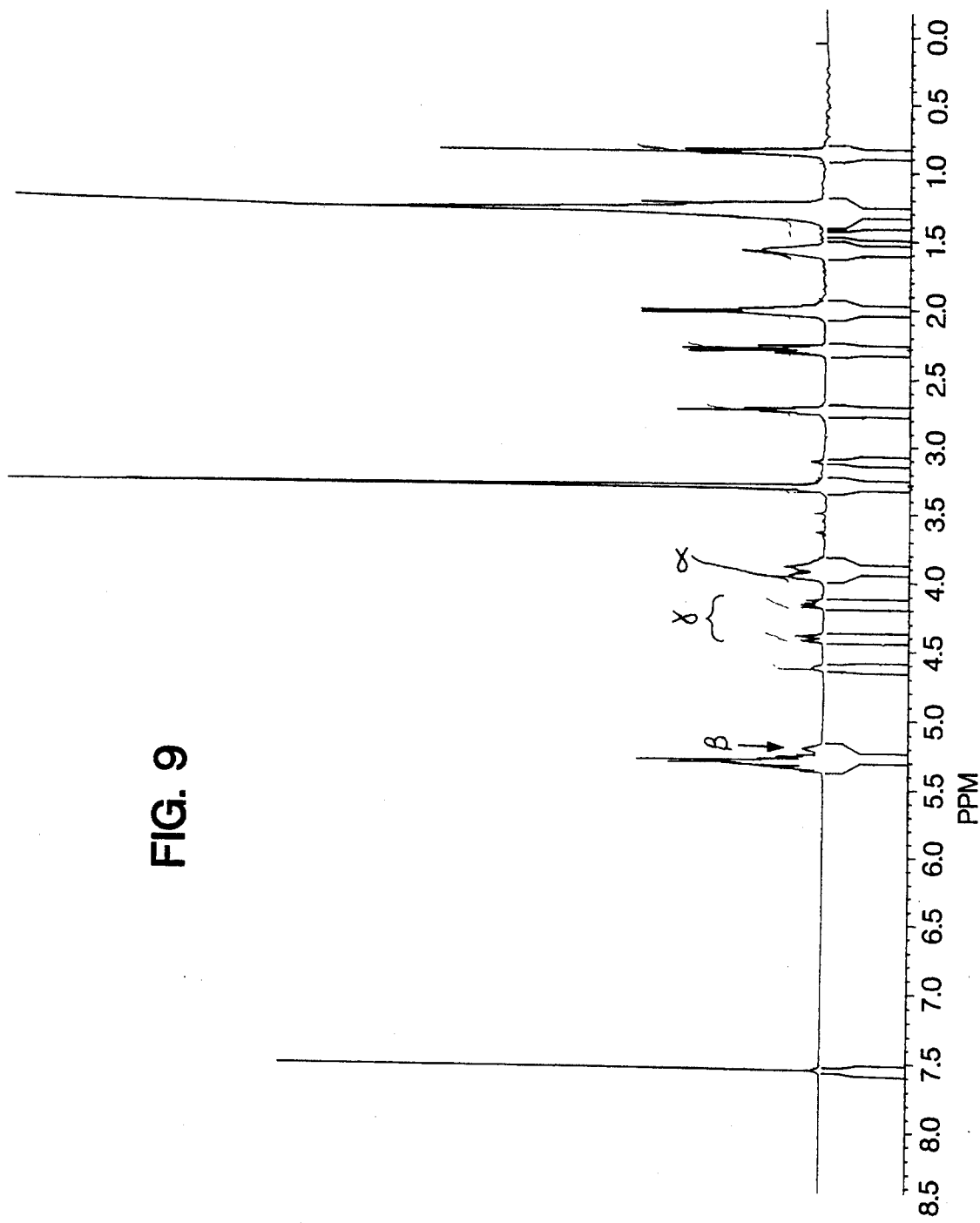
FIG. 9 illustrates the NMR Spectrum of Bovine Heart Cardiolysin.

See FIG. 9 for a reference spectrum for bovine heart cardiolipin (Sigma C5646); to be compared with FIG. 5.

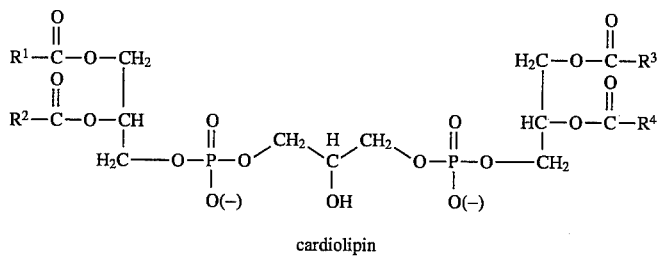

cardiolipin

Analysis of 5

The $^1$H-NMR spectrum of fraction 5 is shown in FIG. 7. The glycerol backbone proton resonances α, β and γ are characteristic of a lysophosphatidic acid core structure, i.e., lacking an acyl chain at the β-hydroxyl function.

Figure 8:
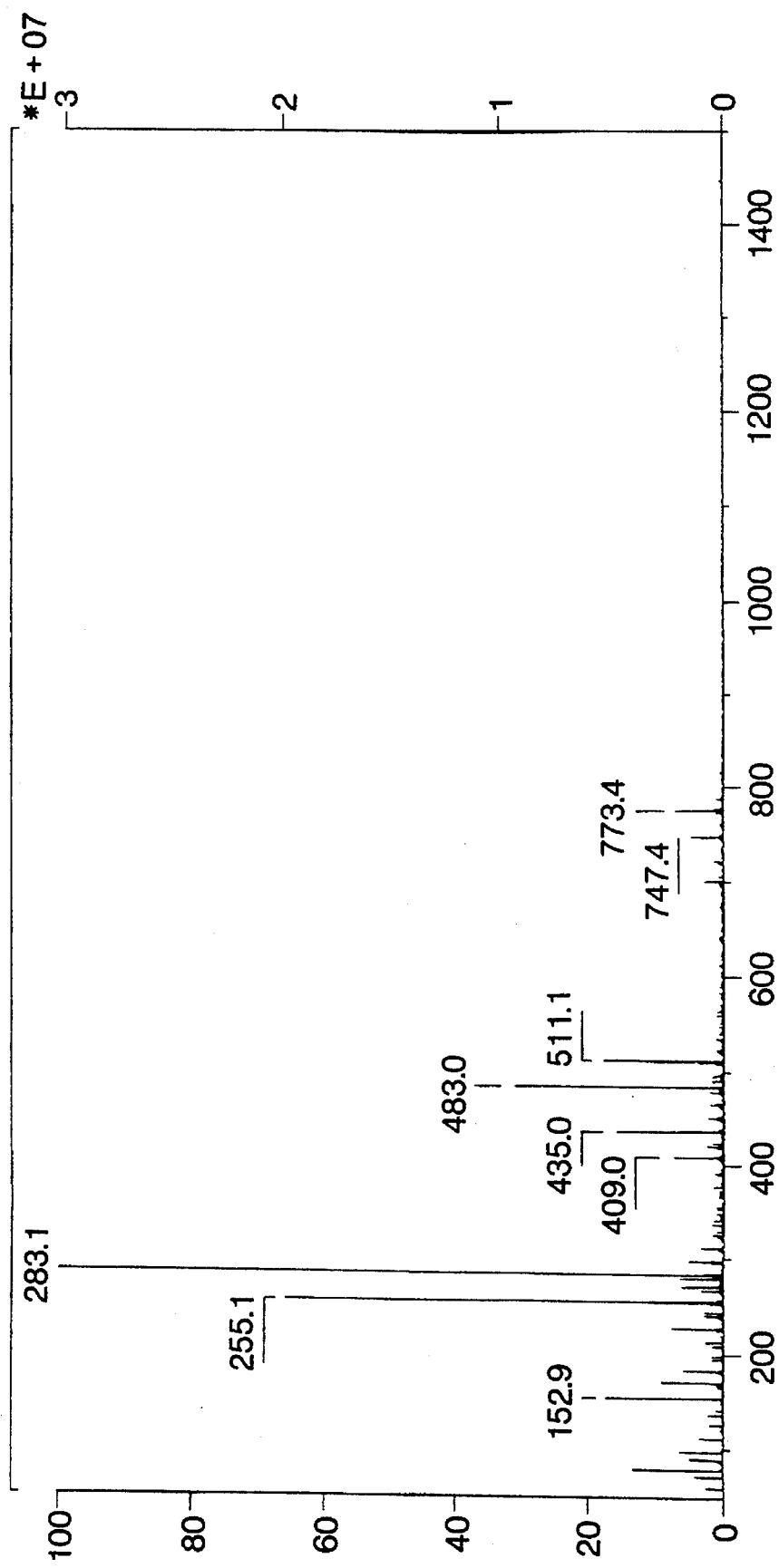
FIG. 8 is the Fast Atom Bombardment (FAB)-Mass Spectrometer Spectra of CTAA 81AV78-5.
Figure 8A:
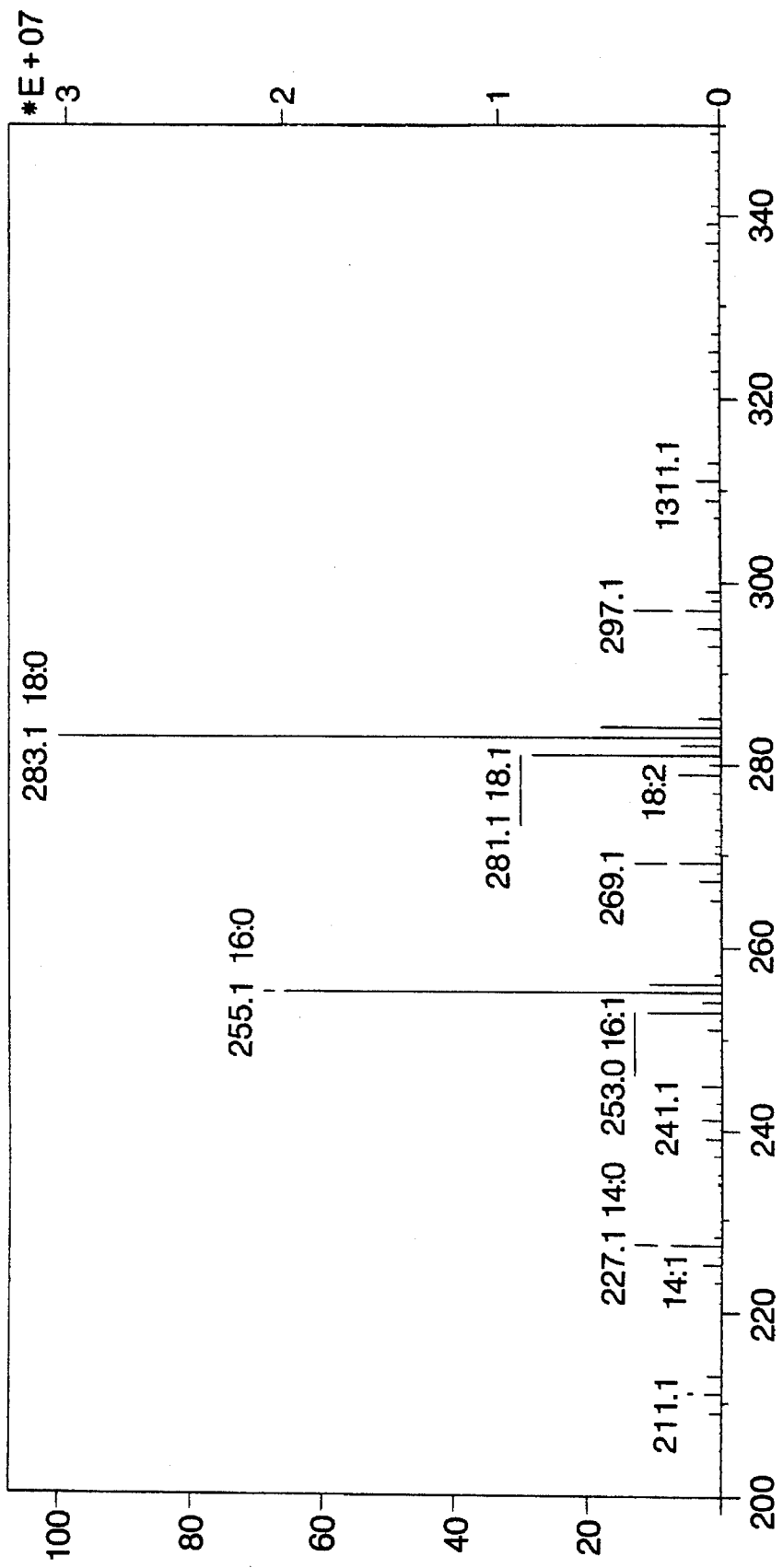
FIG. 8A is an expansion of the region of FIG. 8 between 200 and 350, showing the presence of fatty acids.
Figure 8B:
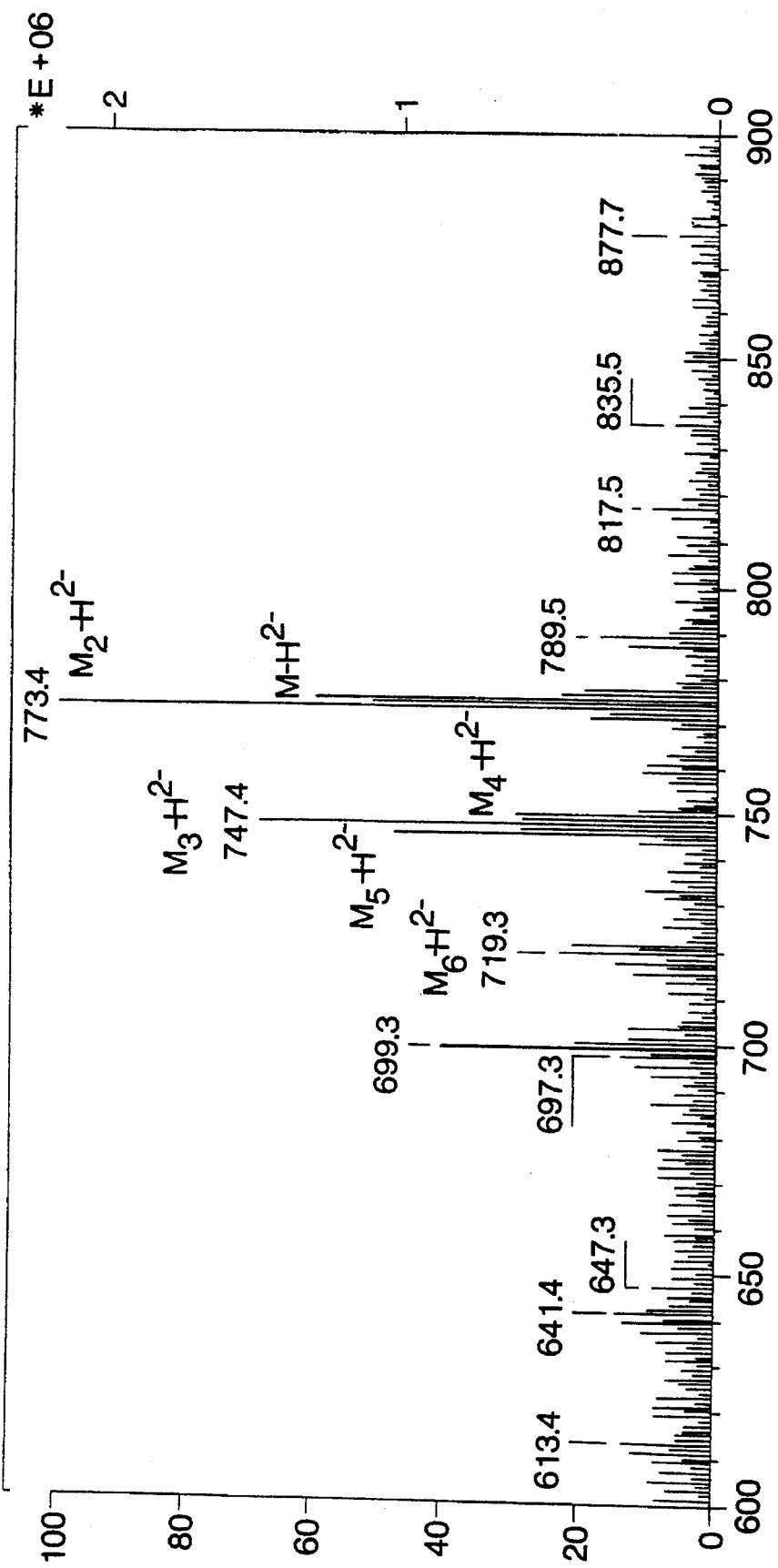
FIG. 8B is an expansion of FIG. 8 between 600 and 900, showing the molecular masses in better detail.

The FAB-MS spectra, reproduced in FIG. 8, provided molecular masses of 744, 748 and 720 (note the mass difference of 28, corresponding to one —$CH_2$—$CH_2$— unit). The following fatty acids were identified: 14:0, 16:0, 16:1, 18:0 and 18:1 FIG. 8a).

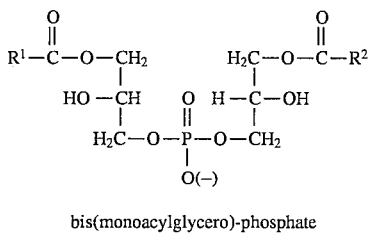

bis(monoacylglycero)-phosphate $^1$H-NMR and FAB-MS were consistent with bis(monoacylglycero) phosphate as the main component in antigen fraction 5, with heterogeneity in the fatty acid part of the molecule.

Figure 10:
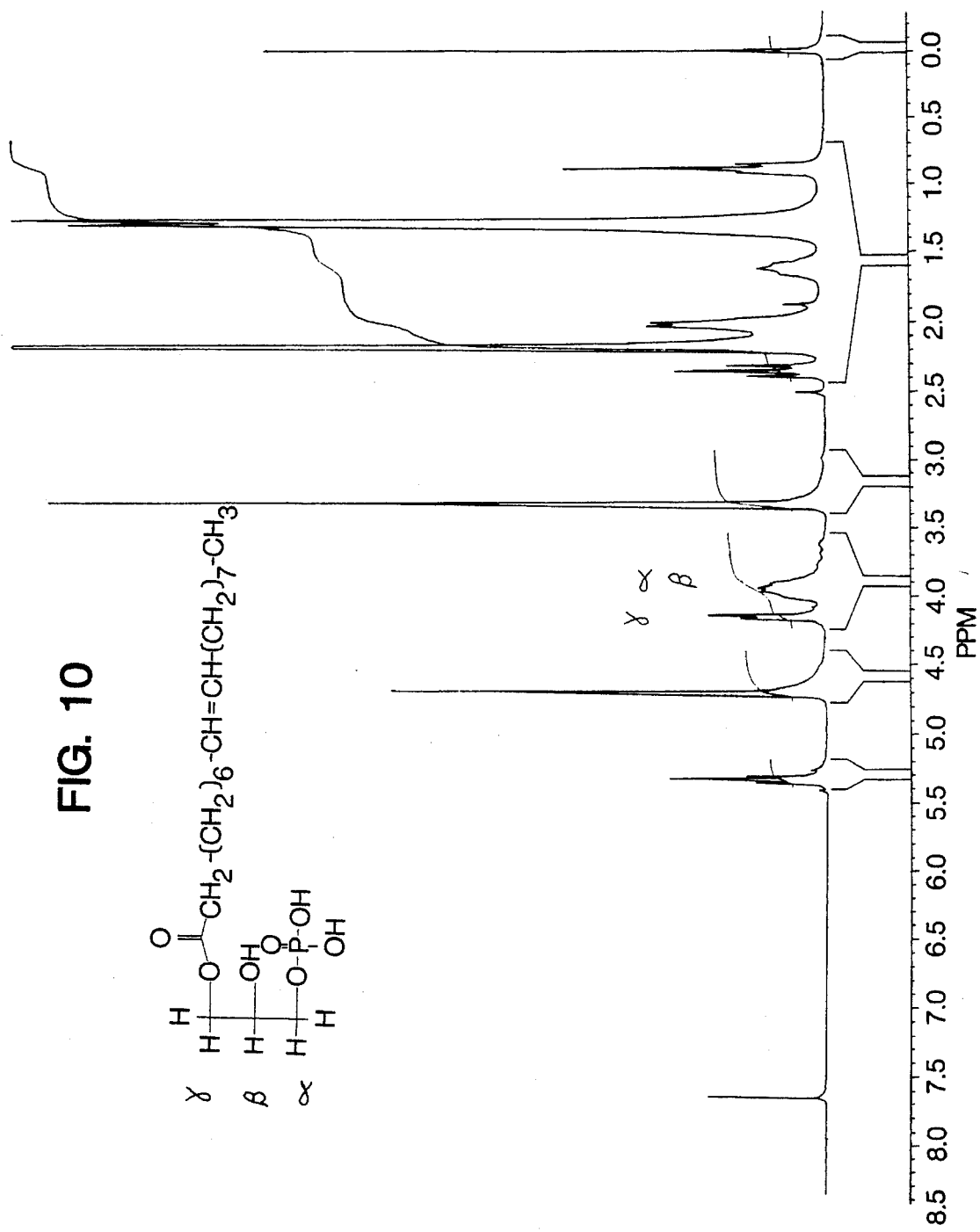
FIG. 10 illustrates the NMR Spectrum of Mono-oleoyl-phosphatidic Acid.

See FIG. 10 for a reference spectrum for mono-oleoyl-lysophosphatidic acid, to be compared ($\alpha$, $\beta$ and $\gamma$ resonances) with FIG. 7.

Fatty Acid Analyses

Samples of fractions 4A and 5 were treated with methanol:$H_2SO_4$. The resulting fatty acid methyl esters were analyzed by a gas-chromatographic method. The results are shown in Table 6. The numbers (duplicate measurements) represent μgrams of fatty acid in the sample. Since the sample weight was unknown, only information on the relative amounts was obtained. The analyses agree with the FAB-MS results with respect to the presence of C-16 and C-18 fatty acid side chains in the phospholipids 4A and 5.

TABLE 1.A.

ONE DIMENSIONAL THIN LAYER CHROMATOGRAPHY OF CTAA 81AV78
CTAA 81AV78-4A

| Form of Sample | Amount Used | Solvent System | $R_f^2$ |
| --- | --- | --- | --- |
| Pure | 40 μg | Chloroform-Methanol | 0.83 |
| Pure | 40 μg | Butanol-Pyridine | 0.13 |
| Pure | 40 μg | Propanol-Hexanol | 0.17 |
| Acidic Pool-HCT-8 cells | 40 μg | Chloroform-Methanol | 0.73 |
| Acidic Pool-HCT-8 cells | 80 μg | Chloroform-Methanol | 0.71 |
| Acidic Pool-HCT-8 cells | 160 μg | Chloroform-Methanol | 0.69 |
| Acidic Pool-HCT-8 cells | 40 μg | Butanol-Pyridine | 0.14 |
| Acidic Pool-HCT-8 cells | 80 μg | Butanol-Pyridine | 0.14 |
| Acidic Pool-HCT-8 cells | 160 μg | Butanol-Pyridine | 0.14 |
| Acidic Pool-WiDr Cells | 40 μg | Chloroform-Methanol | 0.57 |
| Acidic Pool-WiDr Cells | 80 μg | Chloroform-Methanol | 0.55 |
| Acidic Pool-WiDr Cells | 160 μg | Chloroform-Methanol | 0.56 |
| Acidic Pool-WiDr Cells | 40 μg | Butanol-Pyridine | 0.13 |
| Acidic Pool-WiDr Cells | 80 μg | Butanol-Pyridine | 0.13 |
| Acidic Pool-WiDr Cells | 160 μg | Butanol-Pyridine | 0.11 |

$^1$Calculated as follows: $\frac{\text{Distance migrated by antigen}}{\text{Distance of solvent front}}$
$R_f$ is average of 3 samples, values are ±10%

TABLE 1.B.

ONE DIMENSIONAL THIN LAYER CHROMATOGRAPHY OF CTAA 81AV78
(continued)
CTAA 81AV78-5

| Form of Sample | Amount Used | Solvent System | $R_f^2$ |
| --- | --- | --- | --- |
| Pure | 40 μg | Chloroform-Methanol | 0.88 |
| Pure | 40 μg | Butanol-Pyridine | 0.45 |
| Pure | 40 μg | Propanol-Hexanol | 0.32 |
| Acidic Pool-HCT-8 cells | 40 μg | Chloroform-Methanol | 0.83 |
| Acidic Pool-HCT-8 cells | 80 μg | Chloroform-Methanol | 0.81 |
| Acidic Pool-HCT-8 cells | 160 μg | Chloroform-Methanol | 0.78 |
| Acidic Pool-HCT-8 cells | 40 μg | Butanol-Pyridine | 0.53 |
| Acidic Pool-HCT-8 cells | 80 μg | Butanol-Pyridine | 0.52 |
| Acidic Pool-HCT-8 cells | 160 μg | Butanol-Pyridine | 0.51 |
| Acidic Pool-HCT-8 cells | 40 μg | Chloroform-Methanol | 0.82 |
| Acidic Pool-WiDr Cells | 80 μg | Chloroform-Methanol | 0.82 |
| Acidic Pool-WiDr Cells | 160 μg | Chloroform-Methanol | 0.84 |
| Acidic Pool-WiDr Cells | 40 μg | Butanol-Pyridine | 0.48 |
| Acidic Pool-WiDr Cells | 80 μg | Butanol-Pyridine | 0.46 |
| Acidic Pool-WiDr Cells | 160 μg | Butanol-Pyridine | 0.41 |

$^1$Calculated as follows: $\frac{\text{Distance migrated by antigen}}{\text{Distance of solvent front}}$
$R_f$ is average of 3 samples, values are ±10%

TABLE 2

THIN DIMENSIONAL THIN LAYER CHROMATOGRAPHY OF CTAA 81AV78

| | CTAA 81AV78-4A | | CTAA 81AV78-5 | |
| --- | --- | --- | --- | --- |
| Form | Solvent System | $^2R_f$ | Solvent System | $R_f$ |
| Acidic Pool-HCT-8 | Chloroform-Methanol | 0.65–0.75 | C$^1$-M | 0.80 |
| Acidic Pool-HCT-8 | Butanol-Pyridine | 0.20–0.26 | B-P | 0.64 |
| Acidic-WiDr | Chloroform-Methanol | 0.78–0.82 | C-M | 0.81 |
| Acidic-WiDr | Butanol-Pyridine | 0.25–0.31 | B-P | 0.67 |
| Pure | Butanol-Pyridine | 0.56 | B-P | 0.58 |
| Pure | Chloroform-Methanol | 0.25–0.32 | C-M | 0.56–0.61 |

$^1$This first solvent listed indicates the first dimension in which the antigen was chromatographed. The second solvent listed is that used for the second dimension of the chromatograph.
$^2$Calculated as follows: $\frac{\text{Distance migrated by antigen}}{\text{Distance of solvent front}}$
$R_f$ values are ±10%

TABLE 3

PROLIFERATIVE RESPONSES TO CTAA 81AV78 FROM THE PBL OF PATIENTS UNDERGOING ACTIVE SPECIFIC IMMUNOTHERAPY

| | | TIME OF PBL COLLECTION | | | |
| --- | --- | --- | --- | --- | --- |
| | | Third Vaccine (Two Weeks > First) | | Fourth Vaccine (6 month > First) | |
| Patient | Antigen | CPM | S.I.$^2$ | CPM | S.I. |
| 1 | Medium | 260 | 1.0 | 518 | 1.0 |
| | PPD | 215 | 0.82 | 734 | 1.5 |
| | CTAA-81AV78-4A | 316 | 1.2 | 3336 | 6.4 |
| | CTAA-81AV78-5 | 251 | 0.96 | 263 | 0.51 |
| 2 | Medium | 274 | 1.0 | 262 | 1.0 |
| | PPD | 3583 | 13.1 | 4634 | 17.7 |
| | CTAA-81AV78-4A | 627 | 2.3 | 268 | 1.1 |
| | CTAA-81AV78-5 | 318 | 1.2 | 440 | 1.7 |

TABLE 4

REACTIVITY OF HUMAN MONOCLONAL ANTIBODY 81AV78
Indirect Immunofluorescence with Live Tumor Cells[a,d]

| Cell Line | Tumor Type | Fluorescence Intensity[c] | |
|---|---|---|---|
| Ht-29 | Colon Carcinoma | 2+[b] | (100%)[c] |
| SKCO-1 | Colon Carcinoma | 3+ | (70%) |
| WiDr | Colon Carcinoma | — | |
| HCT-8 | Colon Carcinoma | 3+ | (60%) |
| Bt-20 | Breast Carcinoma | — | |
| EP | Breast Carcinoma | 3+ | (50%) |
| MCF-7 | Breast Carcinoma | — | |
| CaLu-1 | Lung Adenocarcinoma | 2+ | (75%) |
| A2780 | Ovarian Carcinoma | — | |
| Ovcar3 | Ovarian Carcinoma | 2+ | (50%) |
| Panc-1 | Pancreatic Carcinoma | 2+ | (60%) |
| WI-38 | Normal Fibroblasts | — | |

[a]Concentration of 81AV78 is 10 μg/ml. Reactivity with a control human IgM at 10 μg is negative on all cells.
[b]Florescence Intensity: 4+ strong, 3+ moderate, 2+ weak to moderate, 1+ weak, − negative.
[c]Percentage of cells showing the indicated fluorescence intensity. Remainder of cells are not fluorescent.
[d]Staining of acetone fixed permeabilized cells shows a filamentous cytoskeletal staining pattern. All cell lines give strong fluorescence staining with acetone fixed cells.
Cell lines available from American Type Culture Collection, Rockville, Maryland.

TABLE 5

CTAA 81AV78 EXPRESSION BY TUMOR CELL LINES

| Cell Lines | 4A | 5 |
|---|---|---|
| HCT-8 | 2 | 3 |
| WIDR | 3 | 2 |
| LS174 | 0 | 0 |
| K562 | 1 | 0 |
| CaLu-1 | 1 | 2–1 |
| SKCO-1 | 1 | 2 |
| Ht-29 | 1–0 | 0 |
| Panc-1 | 3–2 | 1 |

0 = None, 1 = Low, 2 = Medium and 3 = high
Cell lines available from American Type Culture Collection, Rockville, Maryland

TABLE 6

| | Analyses Results | | | |
|---|---|---|---|---|
| | C-16 | C-16:1 | C-18 | C-18:1 |
| 4A | 1.31 | 1.81 | 0.97 | 1.26 |
| | 1.90 | 2.43 | 0.89 | 4.01 |
| 5 | 1.00 | 0.90 | 0.58 | 0.63 |
| | 0.95 | 0.93 | 0.55 | 0.52 |

We claim:

1. An essentially purified and isolated human tumor cell, phosphorylated, nonglycosylated lipid antigen immunoreactive with human monoclonal antibody 81AV78 and found on tumor cell lines SKCO-1, HCT-8, EP, CaLu-1, Ovcar3 and Panc-1.

2. The human tumor cell antigen of claim 1, which is designated CTAA 81AV78-4A.

3. The human tumor cell antigen of claim 1, which is designated CTAA 81AV78-5.

4. An immunogenic composition for inducing a cellular response against tumor antigens, comprising an immuogenically effective amount of a human tumor cell antigen of claim 1 and a pharmaceutically acceptable diluent.

5. The immunogenic composition of claim 4, wherein the human tumor cell antigen is CTAA 81AV78-4A.

* * * * *